United States Patent [19]

Kerschner et al.

[11] Patent Number: 5,274,147

[45] Date of Patent: Dec. 28, 1993

[54] PROCESS FOR PREPARING MANGANESE COMPLEXES

[75] Inventors: Judith Kerschner, Ridgewood, N.J.; Jean H. Koek; Ronald P. Potman, both of Schiedam, Netherlands; Lodewijk Van der Wolf, Vlaardingen, Netherlands

[73] Assignee: Lever Brothers Company, Division of Conopco, Inc., New York, N.Y.

[21] Appl. No.: 909,358

[22] Filed: Jul. 6, 1992

[30] Foreign Application Priority Data

Jul. 11, 1991 [GB] United Kingdom ............... 9115012
Nov. 18, 1991 [GB] United Kingdom ............... 9124474

[51] Int. Cl.$^5$ ............... C07F 13/00; B01J 31/22
[52] U.S. Cl. ............... 556/45; 502/150; 502/160; 502/167; 540/465; 546/2; 548/111; 548/312.7; 548/365.1; 556/46; 556/49
[58] Field of Search ............... 540/465; 546/2; 548/341, 356; 556/45, 46, 49; 502/150, 160, 167

[56] References Cited

U.S. PATENT DOCUMENTS 4,728,455 3/1988 Rerek ............... 252/99
5,153,161 10/1992 Kerschner et al. ............... 502/167

FOREIGN PATENT DOCUMENTS 0306089 3/1989 European Pat. Off.
0369841 5/1990 European Pat. Off.
0458397 11/1991 European Pat. Off.
0458398 11/1991 European Pat. Off.

OTHER PUBLICATIONS

K. Wieghardt, "Journal of the American Chemical Society", 1988, vol. 110, No. 22, p. 7398.
"Journal of the Chemical Society—Chemical Communications", 1985, p. 1145.

Primary Examiner—Mukund J. Shah
Assistant Examiner—Y. N. Gupta
Attorney, Agent, or Firm—Milton L. Honig

[57] ABSTRACT

A process for preparing a dinuclear manganese complex of formula (A)

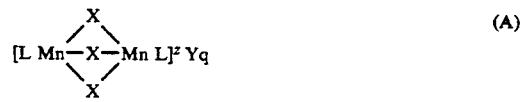

wherein:

Mn represents manganese in the III or IV oxidation state, each X is independently a co-ordinating or bridging species selected from $H_2O$, $O_2^-$, $O^{2-}$, $OH^-$, $SH^-$, $S^{2-}$, $>S=O$, $Cl^-$, $N_3^-$, $SCN^-$, $N^{3-}$, $RCOO^-$, $NH_2^-$ and $NR_3$ where R is hydrogen, alkyl or aryl (optionally substituted);

L is a ligand which is an organic molecule containing at least three nitrogen atoms which coordinate to a manganese centre; Z represents the charge of the complex and is an integer which may be positive or negative;

Y is a monovalent or multivalent counter-ion leading to charge neutrality, which is dependent upon the charge Z of the complex; and q=z/[charge Y], the process comprising the steps of:
(i) reacting an Mn(II) salt with at least an equivalent amount of a compound comprising the ligand L to form said manganese complex characterised in that the reaction is carried out in a non-aqueous solvent; and
(ii) optionally, oxidising the manganese complex formed in step (i) with an oxidising agent.

11 Claims, No Drawings

PROCESS FOR PREPARING MANGANESE COMPLEXES

FIELD OF THE INVENTION

This invention relates to a process for preparing dinuclear manganese complexes. In particular, it relates to a process for preparing manganese(III)- and manganese(IV)-dinuclear complexes usable as bleach catalysts.

THE RELATED ART

Dinuclear complexes of manganese(III) and (IV) and the synthesis thereof have been reported by Karl Wieghardt in the "Journal of the American Chemical Society", 1988, Vol. 110, No 22, pages 7398-7411; and in the "Journal of Chemical Society—Chemical Communications", 1985, pages 347-349. Copending European Patent Specification Nos 458 397 and 458 398 describe dinuclear manganese complexes made by routes similar to those described by Wieghardt.

The synthetic route described in the above art involves reaction, in aqueous medium, of a manganese(III)-compound, for example Mn(III)-triacetate, with a coordinating nitrogen-containing ligand, for example 1,4,7-trimethyl-1,4,7- triazacyclononane, using an ethanol/water mixture as solvent, referred to hereinafter as the complexation step.

A disadvantage of the aforementioned route is that it results in low yields of the dinuclear Mn(III)-complex. A further disadvantage is that, owing to slow crystallization of the desired product, long reaction times are necessary.

Yet a further disadvantage is that decomposition occurs during crystallisation of the desired product yielding manganese dioxide, which contaminates the desired product. Thus, a purification process is required.

Accordingly, it is an object of the present invention to provide an improved method for preparing manganese(III)- and manganese(IV)-dinuclear complexes of the type disclosed in European Patent Specification Nos 458 397 and 458 398.

A more specific object of the present invention is to provide an improved method for preparing dinuclear manganese(III)-complexes of high purity in high yields, which complexes may be converted into the corresponding dinuclear manganese(IV)-complexes by oxidation.

These and other objects of the present invention will become more readily apparent from the detailed description and examples given hereafter.

SUMMARY OF THE INVENTION

It has now been found that high yields of dinuclear Mn(III)- complexes of relatively high purity may be obtained at a much shorter reaction times if the complexation step is carried out under substantially dry conditions.

Accordingly, in its broadest aspect the invention provides a process for preparing dinuclear manganese complexes of the formula (A):

wherein:
Mn represents manganese in the III or IV oxidation state; each X is independently a co-ordinating or bridging species, such as $H_2O$, $O_2^-$, $O^{2-}$, $OH^-$, $HO_2^-$, $SH^-$, $S^{2-}$, $>SO$, $Cl^-$, $N_3^-$, $SCN^-$, $N^{3-}$, $RCOO^-$, $NH_2^-$ or $NR_3$, where R is H, alkyl, or aryl (optionally substituted);
L is a ligand which is an organic molecule comprising at least three nitrogen atoms, which coordinate to a manganese centre;
z represents the charge of the complex and is an integer which can be positive or negative;
Y is a monovalent or multivalent counter-ion, leading to charge neutrality, which is dependent upon the charge z of the complex; and
q=z/[charge Y], the process comprising the step of (i) reaction of an Mn(III)-salt with at least an equimolar amount of a compound containing ligand L, characterized in that the reaction is carried out in a non-aqueous solvent, to form a dinuclear Mn(III)-complex, and, (ii) optionally, followed by oxidation of said dinuclear Mn(III)-complex to form the corresponding dinuclear Mn(IV)-complex.

When Mn is manganese in the III oxidation state, X is preferably a combination of $O^{2-}$ and OAc, where Ac is acetate and, most preferably, one X is $O^{2-}$ and the other two X species are both OAc.

When Mn is manganese in the IV oxidation state, each X is preferably $O^{2-}$.

The counter-ion Y needed for charge neutrality of the complex is generally provided by carrying out the complexation step (i.e. reaction of a Mn salt with a compound comprising ligand L) in the presence of a counter-ion-forming salt. Whilst the type of the counter-ion-forming salt, examples of which include chlorides; sulphates; nitrates; methylsulphates; surfactants, such as alkyl sulphates, alkyl sulphonates, alkylbenzene sulphonates, tosylates; trifluoromethyl sulphonates, perchlorates, $NaBPh_4$ and $KPF_6$, is not critical for the conversion, some salts are more preferred because of product properties or for safety reasons. For example, small counter-ions will produce oily liquids and perchlorates are potentially explosive and could become a severe hazard upon large-scale preparations. Preferred counter-ions are the large molecules for example surfactants, especially the tosylate ion. A particularly preferred counter-ion is $PF_6^-$, which is conveniently obtained from $KPF_6$. Dinuclear manganese(III)- and manganese(IV)- complexes having $PF_6^-$ as the counter-ion are solid crystalline products which are easy to handle and to form into a granulated catalyst product.

DETAILED DESCRIPTION

In a preferred embodiment, the process of the invention comprises formation of an Mn(III)-salt from oxidation of a corresponding Mn(II)-salt with a suitable oxidizing agent, for example a permanganate, such as $KMnO_4$ or hydrogen peroxide, prior to or during the complexation step.

Examples of suitable and preferred Mn(III) and Mn(II) salts are respectively Mn(III) triacetate and Mn(II) diacetate.

Preferably the ligand is an organic cyclic compound containing at least three nitrogen atoms which form part of or are attached to the ring structure.

More preferably, the organic cyclic compound is a macrocyclic structure and, most preferably, at least three nitrogen atoms form part of said macrocyclic structure.

The nitrogen atoms in the ligand may be part of tertiary, secondary or primary amine groups, or part of aromatic ring systems, e.g. pyridines, pyrazoles etc. or combinations thereof.

Examples of suitable ligands in their simplest forms are:

i)
  1,4,7-triazacyclononane;
  1,4,7-triazacyclodecane;
  1,4,7-trimethyl-1,4,7-triazacyclononane;
  1,4,7-trimethyl-1,4,7-triazacyclodecane;
  1,4,8-trimethyl-1,4,8-triazacycloundecane;
  1,5,9-trimethyl-1,5,9-triazacyclododecane;
  1,4-dimethyl-7-ethyl-1,4,7-triazacyclononane.

ii)
  Tris(pyridin-2-yl)methane;
  Tris(pyrazol-1-yl)methane;
  Tris(imidazol-2-yl)methane;
  Tris(triazol-1-yl) methane;

iii)
  Tris(pyridin-2-yl)borate;
  Tris(triazol)-1-yl)borate;
  Tris(imidazol-2-yl)phosphine;
  Tris(imidazol-2-yl)borate.

iv)
  cis-cis-1,3,5-trisamino-cyclohexane;
  1,1,1-tris(methylamino)ethane.

v)
  Bis(pyridin-2-yl-methyl)amine;
  Bis(pyrazol-1-yl-methyl)amine;
  Bis(triazol-1-yl-methyl)amine;
  Bis(imidazol-2-yl-methyl)amine, They may be substituted on amine nitrogen atoms and/or CH$_2$ carbon atoms and/or aromatic rings.

Some examples of preferred ligands are:

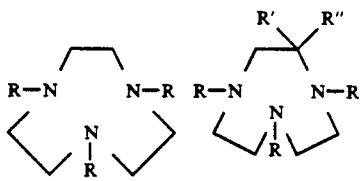

wherein each R is independantly hydrogen or a C$_1$-C$_4$ alkyl group, preferably ethyl most preferably methyl, and R' and R" are independently hydrogen or a C$_1$-C$_4$ alkyl group.

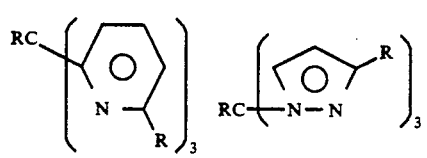

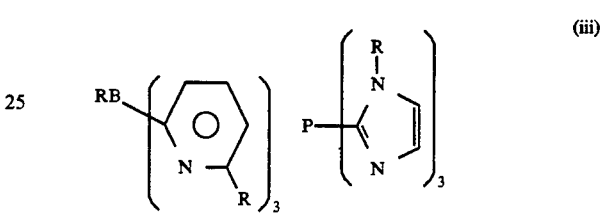

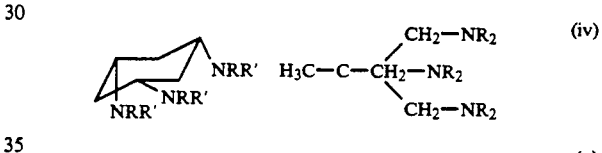

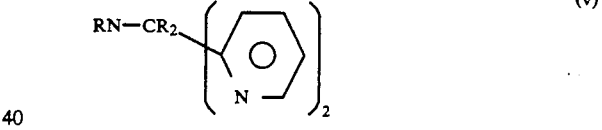

wherein:

R may each independently be H, alkyl, or aryl, optionally substituted; and R' may each independently be hydrogen or alkyl.

A particularly preferred ligand is 1,4,7-trimethyl-1,4,7-triazacyclononane (Me-TACN), which may, for example, form Mn(III)- and Mn(IV)-dinuclear complexes of the following structural formulae:

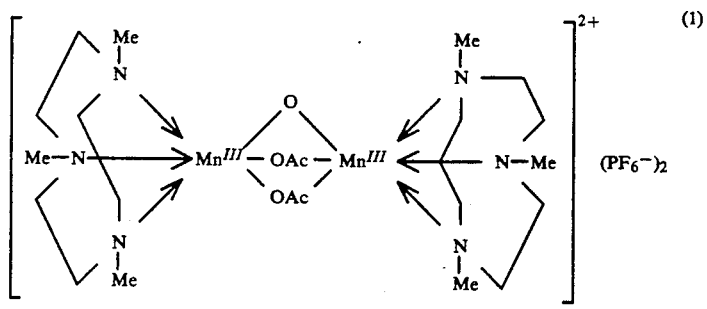

=[(Me-TACN)Mn$^{III}$($\mu$-O) ($\mu$-OAc)$_2$Mn$^{III}$(Me-TACN)](PF$_6$)$_2$, further abbreviated as:

[Mn$^{III}$$_2$($\mu$-O) ($\mu$-OAc)$_2$(Me-TACN)$_2$](PF$_6$)$_2$.

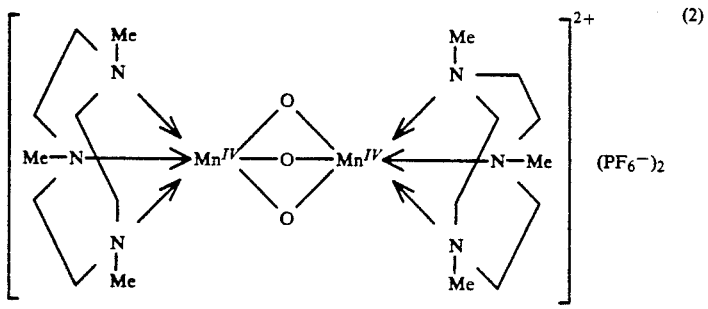

(2)

abbreviated as [Mn$^{IV}$$_2$(μ-O)$_3$(Me-TACN)$_2$](PF$_6$)$_2$.

A further particularly preferred ligand is 1,2,4,7-tetramethyl-1,4,7-triazacyclononane (1,2,4,7-Me$_4$TACN)

Though, in principle, any non-aqueous solvent can be used, polar solvents are preferred. A particularly suitable solvent is acetonitrile.

Preferably the solvent used should be "substantially dry". By "substantially dry", is meant the solvent should contain less than 0.5% by weight of water, preferably less than 0.3% by weight and, most preferably, less than 0.1% by weight.

The temperature at which the reaction is carried out will depend upon the type of ligand and may vary within the range of from about 20° C. up to the boiling temperature of the solvent under the conditions employed, and preferably will be from 20° C. to about 60° C., with a particular preference for a range of 50°-60° C. It has been found the reaction clearly benefits from a higher temperature since higher conversions can be achieved with a shorter reaction time.

As explained, an advantage of the invention is that the reaction produces manganese(III)-dinuclear complexes of high purity in high yields, which may, either directly or after isolation, be converted with a suitable oxidizing agent, for example with air oxygen, to the corresponding manganese(IV)- dinuclear complexes having the same high levels of purity. A further advantage is that, in contrast with the aqueous process of the art, the solvent can be regenerated and recycled for re-use. This is particularly advantageous now that there is a need to reduce the amount of waste products produced during any chemical process.

It is of note that the manganese (IV)-dinuclear complexes e.g. [Mn$^{IV}$$_2$ (μ-O)$_3$ ) (1,4,7-Me$_3$TACN)$_2$] (PF$_6$)$_2$, which will herein-after be referred to as Mn(IV) 1,4,7-Me$_3$TACN complex, are more stable than the corresponding Mn (III) complexes and hence are more suitable for incorporation into bleaching and detergent formulations.

Oxidation of the Mn (III)-dinuclear complex to the corresponding Mn (IV)-complex may be performed by purging air through the reaction system for 18-24 hours followed by filtration and isolation of the Mn (IV)-complex, in about 70% yield. A significant improvement of this oxidation step may be achieved if, instead of air oxygen, pure oxygen or H$_2$O$_2$ (hydrogen peroxide) is used as oxidizing agent. An increased yield is obtained after a much shorter reaction time. The result of oxidizing Mn(III) 1,4,7-Me$_3$TACN-complex to Mn(IV) 1,4,7-Me$_3$TACN complex using different oxidizing agents is illustrated in the following table:

TABLE

| Oxidizing | Yield (approx) | Reaction Time |
|---|---|---|
| Air | 70% | 18-24 hours |
| O$_2$ | 90% | 3-4 hours |
| H$_2$O$_2$ | 90% | 3-4 hours |

According to a preferred embodiment an Mn(III) complex is oxidised to an Mn(IV) complex using substantially pure oxygen or hydrogen peroxide as the oxidising agent.

In the process of the invention a Mn(III)-salt is reacted with a ligand to form a Mn(III)-dinuclear complex. The ligand used in this complexation step may be in its "free form", that is the ligand as such.

It is preferable if the complexation step is carried out in the presence of an effective amount of a strong mineral acid having a pKa <O such as, for example, HCl or H$_2$SO$_4$, which appears to further enhance the conversion. Sulphuric acid is particularly preferred as it will given an even higher yield of final product. The effective amount of strong acid will be from about 0.1:10 equivalent acid to the ligand, preferably from 0.5:5 equivalent acid to ligand. Most preferably, an amount of at least one up to three equivalent acid to ligand is used and immediate addition to the reaction mixture is recommended. Where the ligand is 1,4,7-Me$_3$TACN an amount of acid to give 1,4,7-Me$_3$TACN.3HCl or 1,4,7-Me$_3$TACN.½H$_2$SO$_4$ is preferred, whereby conversions can be increased from about 55% to at least 90%. Alternatively, one may start the complexation step with the salt of the ligand, for example 1,4,7-Me$_3$-TACN.3HCl.

In a further preferred embodiment the reaction incorporates sodium acetate and sodium bicarbonate as an Mn(III) stabilizer and acid scavenger respectively (HCl or H$_2$SO$_4$ comes free during reaction of the chloride or sulphate salts of the ligands with the Mn salt).

The following Examples will more fully illustrate the embodiments of the invention.

EXAMPLES

All solvents were degassed prior to use to exclude oxygen, which oxidizes Mn$^{II}$ to Mn$^{IV}$ and causes the formation of Mn(IV)O$_2$. (Solvent was placed in a vessel and a vacuum applied for 5 minutes. Thereafter, argon gas was introduced into the vessel. This procedure was repeated three times.)

All reactions were carried out at room temperature, under argon, unless otherwise stated.

In the examples 1,4,7-Me$_3$TACN is 1,4,7-trimethyl-1,4,7-triazacyclononane.

COMPARATIVE EXAMPLE

In this example the synthetic route described in the art involving reaction in aqueous medium was used to synthesize:

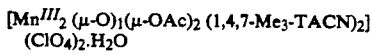
[Mn$^{III}_2$ ($\mu$-O)$_1$($\mu$-OAc)$_2$ (1,4,7-Me$_3$-TACN)$_2$] (ClO$_4$)$_2$.H$_2$O In a 25 ml round-bottomed flask, equipped with a magnetic stirrer, 500 mg (2.91 mmol) 1,4,7-trimethyl-1,4,7-triazacyclononane was dissolved in 15 ml ethanol/water (85/15). This gave a clear, colourless solution (pH>11). 0.45 g (1.80 mmol) Mn$^{III}$(OAc)$_3$.2aq was then added and a cloudy, dark-brown solution was obtained. After addition of 1.00 g (7.29 mmol) NaOAc.3aq, the pH fell to 8. Thereafter about 15 drops of 70% HClO$_4$ solution were added with the result the pH of the reaction mixture fell to 5.0.

After addition of 1.50 g (12.24 mmol) NaClO$_4$, the colour of the reaction mixture changed from brown to red within about 30 minutes. After allowing the reaction mixture to stand for one week at room temperature, the product precipitated in the form of red crystals. The precipitate was filtered over a glass filter, washed with ethanol/water (85/15) and dried in a dessicator over KOH. No further product could be isolated from the filtrate. Yield of Mn$^{III}_2$ complex: 360 mg (=30% based on 1,4,7-Me$_3$-TACN).

EXAMPLE I

Preparation of:

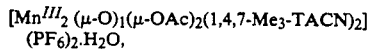
[Mn$^{III}_2$ ($\mu$-O)$_1$($\mu$-OAc)$_2$(1,4,7-Me$_3$-TACN)$_2$] (PF$_6$)$_2$.H$_2$O, under substantially dry conditions starting from Mn(III) acetate and 1,4,7 Me$_3$-TACN.

To a stirred mixture of 420 mg (5 mmol) NaHCO$_3$$^{c)}$, 410 mg (5 mmol) NaOAc $^{c)}$ (Na-acetate), 460 mg (2.5 mmol) KPF$_6$ and 536 mg (2 mmol) Mn$^{III}$(OAc)$_3$.2H$_2$O in 25 ml acetonitrile in a graduated Schlenk tube under argon; 2 mmol 1,4,7-Me$_3$TACN$^{a)}$ (0.5 mmol/ml in acetonitrile) was added. Stirring at 60° C. (bath) was continued for 1 hour. 55% conversion was obtained$^{d)}$. The reaction mixture was cooled down and filtered. After evaporation (30° C., vacuum) of the filtrate a viscous dark red brown product was obtained. Upon addition of about 25 ml water with stirring and while evacuating, the residue turned into a crystalline product, which was collected on a glass fritt, washed with water and dried (vacuum and argon stream) until constant weight. Yield: 701 mg (78%); Purity (UV/VIS) 77%, giving a corrected yield of 61%.

$^{a)}$ Obtained by adding 0.235 mol EtONa, dissolved in 200 ml EtOH, to a stirred suspension of 21.0 g (75 mmol) 1,4,7-Me$_3$-TACN.3.HCl$^{b)}$ at room temperature under argon. After stirring for 2 hours the reaction mixture was filtered and the resulting filtercake washed with methanol and dicholormethane. After evaporation of the combined filtrates the residue was distilled. Yield 7.36 g (57%) with b.p. 55°–57°/0.1 mmHg. $^1$H—NMR: 2.35 (s), N—CH$_3$ and 2.63 (s), N—CH$_2$CH$_2$—N. The remainder was transferred to a graduated Schlenk tube and dissolved in acetonitrile (c=0.5 mmol/ml) and stored in a refrigerator under argon.

$^{b)}$ Prepared according to K Wieghardt, Chem. Ber, 112, page 2228, 1979.

$^{c)}$ Finely powdered.

$^{d)}$ The conversion was measured by UV/Vis spectroscopy. An aliquot (usually 250 or 300 $\mu$l) was filtered directly into a 50 ml standard flask with acetonitrile (by pressuring with argon). The resulting solution was used for measuring and calculating the conversion by taking the molar extinction coefficient of the Mn$^{III}_2$- complex at 310 nm as 14000.

$^{e)}$ From 1,2-propyleneglycol-ditosylate (prepared according R W Hay; J Chem Soc Dalton Trans. 1441–1445 (1979) and diethylenetriamine-N,N',N'' tritosylate (prepared via R W Hay idem) the 2-methyl-1,4,7-tritosyl-TACN was prepared and detosylated giving 2-Me-TACN according to the method of K Weighardt, Chem Ber. 112, p 2220–2230. The 2-Me-TACN was methylated giving 1,2,4,7-Me$_4$TACN using Weighardt's method, Inorg. Chem. 21, 3086–3090 (1979).

$^{f)}$ from 2-methyl-1,2-diaminopropane-N,N'-ditosylate and diethanolamine-N,O,O'-tritosylate the 2,2-dimethyl-1,4,7-Tos$_3$TACN was prepared. Subsequent detosylation (according to D Dischino, Inorg. Chem. 30. 1265–1269 (1991) using dissolving sodium in liquid ammonia in the presence of urea gave the 2,2-Me$_2$-TACN. The latter was converted to 1,2,2,4,7-Me$_5$TACN using the methylation method described in $^{e)}$ above.

$^{g)}$ 1,4-Me$_2$TACN.2HBr; prepared according to C Flassbeck and K Wieghardt. Z. Anorg. Allg. Chem 608, 60–68 (1992).

$^{h)}$ Prepared from TACN.3HBr using the method described by G W Gribble, P D Lord, J Skotnicki, S E Dietz, J T Eaton and J L Johnson; J. Am. Chem. Soc. 96, 7812 (1974).

$^{i)}$ Via the ethylation procedure described above in $^{h)}$ using as substrate 1,4-Me$_2$TACN.3HBr.

EXAMPLE II

Preparation of:

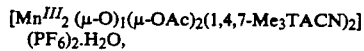
[Mn$^{III}_2$ ($\mu$-O)$_1$($\mu$-OAc)$_2$(1,4,7-Me$_3$TACN)$_2$] (PF$_6$)$_2$.H$_2$O, where Me-TACN is 1,4,7-trimethyl-1,4,7-triazacyclononane, under substantially anhydrous conditions from Mn(III)-triacetate and 1,4,7-Me$_3$TACN.3HCl.

561 mg (2 mmol) 1,4,7-Me$_3$-TACN.3HCl$^{b)}$, 420 mg (5 mmol) NaHCO$_3$, 410 mg (5 mmol) NaOAc, 460 mg (2.5 mmol) KPF$_6$ were stirred with 30 ml acetonitrile (degassed) under argon. After addition of 536 mg (2 mmol) Mn$^{III}$(OAc)$_3$2H$_2$O, the temperature was raised gradually to 55° C. over a period of 30 minutes and stirring was continued for 2.5 hours at that temperature. Within a few minutes, the brownish coloured suspension turned to brownish purple, via dark-greyish brown. After filtration, the conversion, as measured by UV/VIS, proved to be 95%. Evaporation (30° C., vacuum) of the filtrate, stirring the residue with water, collecting the solidified products on a glass funnel, washing with water and drying (vacuum and argon) yielded 659 mg (74%) of the $Mn^{III}_2$ complex.

Purity 100% (UV/VIS extinction 14,000 at 310 nm). On evaporation of the green-coloured filtrate and flushing the residue (275 mg) with argon overnight, the reddish colour reappeared. Upon stirring this residue with water an additional portion of the complex was obtained (60 mg; 7%; purity 65%), giving a total yield of 79%.

EXAMPLE III

Preparation of:

[$Mn^{III}_2$ (μ-O)$_1$(μ-OAc)$_2$(1,4,7-Me$_3$-TACN)$_2$] (PF$_6$)$_2$.H$_2$O using KMnO$_4$ and Mn(II)-diacetate in dry acetonitrile.

Amounts of 392 mg (1.6 mmol) $Mn^{II}(OAc)_2.4H_2O$, 63 mg (0.4 mmol) KMnO$_4$ and 0.16 ml (6 mmol) acetic acid were stirred and refluxed for 0.5 hours in 40 ml of acetonitrile. The mixture was intensely brown-coloured (formation of $Mn^{III}(OAc)_3$). It was allowed to cool to 25° C. Then a mixture of 561 mg (2 mmol) 1,4,7-Me$_3$-TACN.3HCl[b], 420 mg (5 mmol) NaHCO$_3$, 410 mg (5 mmol) NaOAc and 460 mg (2.5 mmol) KPF$_6$ was added in one batch to the reaction mixture. The resulting reaction mixture was stirred and refluxed for 30' (After 15', % conversion to $Mn^{III}_2$ complex was measured using UV/VIS spectroscopy. A figure of 80% was obtained. The mixture was allowed to cool to 25° C., filtered and the filtrate evaporated to 4 ml (10% of its original volume). To this concentrate, 50 ml of water was added and the product crystallized. Upon filtration, the product was isolated and after drying 0.77 g (86%) yield of purple powder was obtained which, according to UV/VIS spectroscopy, was 90% pure.

EXAMPLE IV

Preparation of:

Dinuclear Mn(III) 1,4,7-Me$_3$-TACN complex starting from Mn(III) acetate and Me-TACN in presence of H$_2$SO$_4$. 2 mmol Me-TACN (0.5 mmol/ml in acetonitrile)[a] was added to 25 ml acetonitrile in a graduated Schlenk tube under argon. Thereafter, 110 μl (2 mmol) H$_2$SO$_4$ was added by means of a syringe. Initially a sticky precipitate formed but this then went into solution. After stirring for 10 minutes 420 mg (5 mmol) NaHCO$_3$[c], 410 mg (5 mmol) NaOAc[c], 460 mg (2.5 mmol) KPF$_6$ and 536 mg (2 mmol) Mn(OAc)$_3$.2 H$_2$O were added simultaneously while stirring at room temperature. During stirring at 60° (bath) the conversion was monitored by UV/VIS spectroscopy[d]. After 0.5 h and 1 h conversions of 96 and 92% respectively were determined! The reaction mixture was then cooled down and filtered into a graduated flask or a standard flask and the conversion again measured. This gave a figure of 90%. After evaporation (30° C., vacuum) of the filtrate a viscous dark red brown product was obtained. About 25 ml water was added with stirring. While evacuating, the residue turned into a crystalline product, which was collected on a glass fritt, washed with water and dried (vacuum and argon stream) until constant weight. Yield: 767 mg (86%); Purity (UV/VIS): 100%.

EXAMPLE V

Preparation of:

[$Mn^{IV}_2$ (μ-O)$_3$(1,4,7-Me$_3$-TACN)$_2$](PF$_6$)$_2$.H$_2$O

In a 50 ml round bottomed flask provided with a magnetic stirrer, 661.4 mg of the dinuclear Mn(III) 1,4,7 Me$_3$-TACN complex crystals as obtained from Example I (0.823 mmol) pulverized as a purple powder, were dissolved in 40 ml of a 1:1 ethanol/water mixture. After five minutes ultrasonic treatment and 15 minutes stirring at room temperature, all the powder was dissolved giving rise to a dark red coloured neutral solution. 4 ml of triethylamine was added and the reaction mixture turned to a dark brown colour (pH>11). After 15 minutes of stirring at room temperature in the presence of air the mixture was filtered to remove some manganese dioxide and the filtrate was allowed to stand overnight. A mixture of MnO$_2$ and red crystals were formed. The solids were collected by filtration and washed with ethanol. The red needle-like crystals were isolated by adding a few ml of acetonitrile to the filter. The crystals easily dissolved, while MnO$_2$, insoluble in acetonitrile, remained on the filter. Evaporation of the acetonitrile solution gave a product as red flocks. The ethanol/water filtrate was evaporated a little and kept in a refrigeration overnight eventually giving more product. This procedure was repeated a few times until no more product crystallized from the filtrate. The overall yield was 450 mg (68%). The UV/Vis spectra of the product in acetonitrile and water was measured.

UV (CH$_3$CN): lambda max. (extinction; extinction coefficient according literature (JACS, 1988, vol 110, No 22, pages 7398-7411); 213 nm (sh); 235 mn (18300, 18000); 270 nm (15300, 16000); 313 nm (8600, 9400); 394 nm (817, 1300); 492 nm (491, sh).

UV (H$_2$O): lambda max. (extinction): 200 nm (18600); 244 nm (19300); 278 nm (18600); 313 nm (12000); 389 nm (1100); 483 nm (465).

IR (KBr): 3600 & 34000 cm$^{-1}$ (water); 2900-3000 cm$^{-1}$ (C—H); 1640 & 840 cm$^{-1}$ (PF$_6$—); 1010 cm$^{-1}$ (C—N); 750 cm$^{-1}$ (Mn—O—Mn).

Elemental analysis of [L$_2$Mn$^{IV}_2$(μ-O)$_3$](PF$_6$)$_2$.H$_2$O; C: 26.90% (calcd. 26.74%); H: 5.49% (calcd. 5.50%); N: 10.26% (calcd. 10.40%); Mn: 13.7% (calcd. 13.59%); P: 7.77% (calcd. 7.66%); F: 28.73% (calcd. 28.20%).

EXAMPLE VI

Preparation of:

[$Mn^{III}_2$(μ-O)$_1$ (μ-OAc)$_2$(1,4,7-Me$_3$-TACN)$_2$](PF$_6$)$_2$.H$_2$O, using Mn(II)-diacetate/KMnO$_4$, Me-TACN(H$_2$SO$_4$)$_\frac{1}{2}$.

To a magnetically stirred 2-necked reaction flask, provided with a jacket that enabled temperature control, containing a suspension of 1025 mg (12.5 mmol) NaOAc and 1078 mg (4.4 mmol) Mn(OAc)$_2$.4H$_2$O in 25 ml acetonitrile was added 503 μl (8.8 mmol) AcOH followed by 174 mg (1.1 mmol) KMnO$_4$. After stirring for 45 min at room temperature 1150 mg (6.25 mmol) KPF$_6$ and 420 mg (5 mmol) NaHCO$_3$ was added. Meanwhile a solution of 140 μl (2.5 mmol) H$_2$SO$_4$-96% in 15 ml acetonitile, prepared in a Schlenk tube, was transferred to a second Schlenk tube that contained a stirred solution of 5 mmol 1,4,7 Me$_3$-TACN [a] in 20 ml acetonitrile. When the resulting thready and sticky precipitate had been dissolved, the 1,4,7-Me$_3$-TACN (H$_2$SO$_4$)$_\frac{1}{2}$ containing solution obtained was transferred immediately to the Mn(III)-acetate containing reaction flask. Subsequently the reaction mixture was stirred thermostatically at 55° for 3 hours while monitoring the progress of the complex formation by UV/VIS spectroscopy (see Example IV). The data obtained showing the variation of % conversion with time is as follows: 20′: 76%; 40′: 89%; 1h: 91.5%; 2h: 90.5%; 2.5h: 91% and 3h: 92%.

After 3 hours, the reaction mixture was cooled down to about 20° C. and filtered into a graduated cylindrical flask. A conversion of 88.3% was measured.

Upon rota-evaporation (30° C., vacuum) of the filtrate the dark reddish brown coloured viscous product was stirred with about 25 ml water and again evacuated. In this way the residue turned into a dark purple solid which was collected on a frit, washed with small portions of water (three times) and ether. Drying until constant weight (vacuum and argon stream overnight).

Yield: 1976 mg (88.4%)
Purity (UV/VIS): 94%.

EXAMPLE VII

Preparation of:

[Mn$^{IV}$$_2$($\mu$-O)$_3$(1,4,7-Me$_3$-TACN)$_2$](PF$_6$)$_2$.H$_2$O To a 4 ml acetonitrile solution of [Mn$^{III}$$_2$($\mu$-O) ($\mu$-OAc)$_2$(1,4,7-Me$_3$-TACN)$_2$](PF$_6$)$_2$.H$_2$O (7.79 mmol) in a 250 ml flask was added 160 ml of ethanol/water (50:50) followed by the addition of 30 ml triethylamine. The reaction mixture turned brown upon addition of the amine. To the resulting suspension was slowly added 2.34 ml 30% H$_2$O$_2$(23.23 mmol). (Slow addition is required to prevent excessive foaming) and the reaction mixture was stirred at room temperature for 5 hours.[1] The red solution was then immediately filtered to remove brown MnO$_2$ byproduct, and the filtrate was concentrated to 1/10 volume in vacuo causing precipitation of the red crystalline [Mn$^{IV}$$_2$($\mu$-O)$_3$ (1,4,7-Me$_3$-TACN)$_2$] (PF$_6$)$_2$.H$_2$O. The crystals were then isolated by filtration and washed with ethanol and ether. The red solid was dried in vacuo (40°-50° C.) yielding 5.15 g (82% yield based on Mn (III) complex). The solution can be further concentrated to yield more Mn(IV)$_2$ complex in lower purity. (Purity is lowered by the presence of excess salts).

UV/Vis (CH$_3$CN - 1.2e-4M) lambdamax (extinction, extinction - lit.): 235 nm (18370, 18000), 270 nm (15920, 1600), 313nm (9510, 9400), 385nm (955, 1300), 490 nm (sh).

HPLC Separation: C-18 Reverse Phase Column—15 cm (Regis)
Mobile Phase 85:15 pH3 buffer: CH$_3$CN
pH3 Buffer-20 ml stock solution diluted to 1 liter
Flow Solution
8 ml H$_3$PO$_4$(conc.)
10 ml Et$_3$N
water to 100 ml
Flow rate—1 ml/min (20 $\mu$l injection vol.)
Diode Array Detector—230, 240 and 313 nm
Sample Concentration—25-1000 ppm.

1. The oxidation can be performed by purging the solution with pure oxygen or air with reaction time of 3.5 hours or 18-24 hours, respectively. The yield of the oxygen oxidation was 86-90%. The yield for the air oxidation was only about 70% possibly due to decomposition of the Mn(IV) complex which occurs due to the instability of the complex in basic solutions (over several hours).

EXAMPLE VIII

Preparation of:

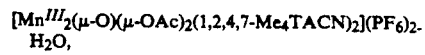
[Mn$^{III}$$_2$($\mu$-O)($\mu$-OAc)$_2$(1,2,4,7-Me$_4$TACN)$_2$](PF$_6$)$_2$.H$_2$O, under substantially anhydrous conditions from Mn$^{III}$ triacetate and 1,2,4,7-Me$_4$TACN.3HCl.

Example II was repeated except the 1,4,7-Me$_3$-TACN.3HCl was replaced by 589 mg (2mmol) of 1,2,4,7-Me$_4$TACN.3HCl$^{e)}$.

The UV/Vis spectrum of the material obtained was measured:

| lambdamax { molar extinction coefficient } | : | 310 nm (13200); 485 nm (640); 521 nm (635); 720 nm (110). |
|---|---|---|

EXAMPLE IX

Preparation of:

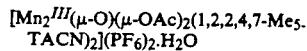
[Mn$_2$$^{III}$($\mu$-O)($\mu$-OAc)$_2$(1,2,2,4,7-Me$_5$-TACN)$_2$](PF$_6$)$_2$.H$_2$O under substantially anhydrous conditions from Mn$^{III}$ triacetate and 1,2,2,4,7-Me$_5$TACN.3HCl.

Example II was repeated except the 1,4,7-Me$_3$-TACN.3HCl was replaced by 617 mg (2mmol) of 1,2,2,4,7-Me$_3$TACN.3HCl$^{f)}$.

The UV/Vis spectrum of the material obtained was measured:

| lambdamax { molar extinction coefficient } | : | 309 nm (8900); 487 nm (490); 523 nm (610). |
|---|---|---|

EXAMPLE X

Preparation of:

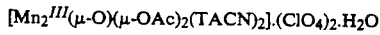
[Mn$_2$$^{III}$($\mu$-O)($\mu$-OAc)$_2$(TACN)$_2$].(ClO$_4$)$_2$.H$_2$O under substantially anhydrous conditions from Mn$^{III}$ triacetate and TACN.3HBr.

630 mg (2 mmol) TACN.3HBr$^{b)}$, 386 mg (4.6 mmol), NaHCO$_3$ $^{c)}$, 410 mg (5 mmol) AcONa, 1224 mg (10 mmol) NaClO$_4$, and 536 mg (2 mmol), Mn(OAc)$_3$.2H$_2$O in 30 ml acetonitrile were stirred under argon at 55° C. Within a few minutes the brown coloured mixture darkened while the suspension grew thinner. After 1 hour the flask contents were cooled and filtrated. Then the filtrate was evaporated partly (vacuum). Subsequently ethanol was evaporated partly. Addition of a saturated solution of NaClO$_4$ in ethanol initiated crystallization. After standing overnight the resulting complex was collected on a frit, washed with ethanol and ether, and dried under argon. Yield: 512 mg (73%).

UV/Vis in CH$_3$CN, lambda max (nm)/($\epsilon$): 230 (9030), 274 (10.250), 300 (sh), 372 (sh), 484 (375), 518 (290), 541 (sh), 560 (sh) and 660 (120).

EXAMPLE XI

Preparation of:

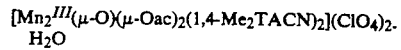
[Mn$_2$$^{III}$($\mu$-O)($\mu$-Oac)$_2$(1,4-Me$_2$TACN)$_2$](ClO$_4$)$_2$.H$_2$O under substantially anhydrous conditions from $Mn^{III}$triacetate and 1,4-Me$_2$TACN.3HBr.

Example X was repeated except:
i) 900 mg 1,4-dimethyl-TACN.3HBr$^g$) was used in replace of the TACN.3HBr;
ii) the reaction was carried out at room temperature for 2.5 hours.

The resulting precipitate in ethanol was (re) crystallized by adding small amounts of acetonitrile to dissolve it and, subsequently, adding a solution of NaClO$_4$ in ethanol. In this way 288 mg (38%) of the compound was obtained. UV/Vis in CH$_3$CN, lambda max(nm)/($\epsilon$): 241 (9600), 282 (sh), 298 (130000), 386 (sh), 484 (485), 517 (410), 542 (sh), 560 (sh) and 680 (110).

EXAMPLE XII

Preparation of:

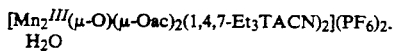

[Mn$_2^{III}$($\mu$-O)($\mu$-Oac)$_2$(1,4,7-Et$_3$TACN)$_2$](PF$_6$)$_2$.H$_2$O under substantially anhydrous conditions from $Mn^{III}$triacetate and 1,4,7-Et$_3$TACN.3HCl.

Example II was repeated except the 1,4,7-Me$_3$-TACN.3HCl was replaced by 645 mg (2mmol) of 1,4,7-Et$_3$TACN.3HCl$^h$). A much longer reaction time (about 2 days) was required.

The UV/Vis spectrum of the material obtained was measured:

| lambdamax ($\epsilon$): | 318 nm (13300); 485 nm (702); |
| --- | --- |
| | 522 nm (716); 729 nm (130). |

EXAMPLE XIII

Preparation of:

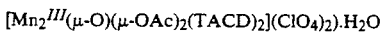

[Mn$_2^{III}$($\mu$-O)($\mu$-OAc)$_2$(TACD)$_2$](ClO$_4$)$_2$).H$_2$O under substantially anhydrous conditions from $Mn^{III}$triacetate andTACD.3HBr, where TACD is 1,4,7-triazacyclodecane.

Example X was repeated except TACN.2.3HBr was replaced by 589 mg (2 mmol) of TACD.3HCl$^b$).

UV/Vis in CH$_3$CN:

| lambdamax ($\epsilon$): | 278 nm (9700); 483 nm (320); |
| --- | --- |
| | 515 nm (716); 640 nm (160). |

EXAMPLE XIV

Preparation of:

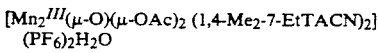

[Mn$_2^{III}$($\mu$-O)($\mu$-OAc)$_2$ (1,4-Me$_2$-7-EtTACN)$_2$](PF$_6$)$_2$H$_2$O under substantially anhydrous conditions from $Mn^{III}$ triacetate and 1,4-Me$_3$-7-EtTACN.3HCl.

Example II was repeated except the 1,4,7-Me$_3$-TACN.3HCl was replaced by 645 mg (2 mmol) of 1,4,-Me$_2$-7-EtTACN.3CHl$^i$).

The UV/Vis spectrum of the material obtained was measured:

| Lambdamax ($\epsilon$): | 311 nm (14200); 485 nm (741); |
| --- | --- |
| | 521 nm (719); 725 nm (100). |

EXAMPLE XV

Preparation of:

[Mn$^{IV}_2$($\mu$-O)$_3$(1,2,2,4,7-Me$_5$TACN)$_2$](PF$_6$)$_2$H$_2$O.

To a solution of 202 mg (0.217 mmol) [(1,2,2,4,7-pentamethyl-TACN)$_2$Mn$_2^{III}$($\mu$-0) ($\mu$-OAc)$_2$] (PF$_6$)$_2$ in 4.2 ml ethanol/water (1:1) was added 745 $\mu$l (5.35 mmol) triethylamine. Oxygen was then bubbled through the solution for 4.5 h at room temperature. After filtration, the filtrate was evaporated, the residue dissolved in acetonitrile/water (2:1) and again filtrated. Upon addition of ethanol and ether the complex crystallized. Yield: 12 mg (6.4%).

UV/Vis in CH$_3$CN:

| lambdamax ($\epsilon$): | 239 nm (15950) 275 nm (14050) |
| --- | --- |
| | 316 nm (9340) 391 nm (890) |
| | 494 nm (400). |

Crystallization of the concentrated filtrate from an ethanolic solution of NaClO$_4$ yielded a second crop of 9 mg (5.4%) of Mn$_2^{IV}$-complex.

EXAMPLE XVI

Preparation of:

[Mn$^{IV}_2$($\mu$-0)$_3$(1,4,7-Et$_3$TACN)$_2$](PF$_6$)$_2$H$_2$O.

Example XV was repeated except [Mn$_2^{III}$($\mu$-0)($\mu$-OAc)$_2$(1,4,7-Et$_3$TACN)$_2$](PF$_6$)$_2$H$_2$O was used.

UV/Vis in CH$_3$CN:

| lambdamax ($\epsilon$): | 245 nm (13500); 279 nm (12900); |
| --- | --- |
| | 317 nm (9200); 387 nm (shoulder, 1000) |
| | 488 nm (350). |

EXAMPLE XVII

Preparation of:

[Mn$_2^{IV}$($\mu$-O)$_3$(1,2,4,7-Me$_4$TACN)$_2$](PF$_6$)$_2$H$_2$O.

Example VII was repeated except [Mn$_2^{III}$($\mu$-0)($\mu$-OAc)$_2$(1,2,4,7-Me$_4$TACN)$_2$]$^{2+}$(PF$_6$)$_2$H$_2$ was used.

UV/Vis in CH$_3$CN:

| lambdamax ($\epsilon$): | 238 nm (18800); 272 nm (16700); |
| --- | --- |
| | 314 nm (9700); |
| | 396 nm (770); 495 nm (330) |

EXAMPLE XVIII

Preparation of:

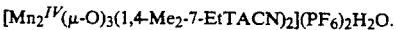

[Mn$_2^{IV}$($\mu$-O)$_3$(1,4-Me$_2$-7-EtTACN)$_2$](PF$_6$)$_2$H$_2$O.

Example XV was repeated except [Mn$_2^{III}$($\mu$-O)($\mu$-OAc)$_2$(1,4,-Me$_2$-7-EtTACN)$_2$](PF$_6$)$_2$H$_2$O was used.

UV/Vis in CH$_3$CN:

| lambdamax (ε): | 238 nm (17200); 273 nm (15350); |
| | 314 nm (9070); 395 nm (865); |
| | 492 nm (345). |

What is claimed is:

1. A process for preparing a dinuclear manganese complex of formula (A):

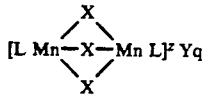

wherein:

Mn represents manganese in the III or IV oxidation state, each X is independently a coordinating or bridging species selected from $H_2O$, $O_2^-$, $O_2$, $OH^-$, $SH^-$, $S_2^- > S=O$, $Cl^-$, $N_3^-$, $SCN^-$, $N^{3-}$, $RCOO^-$, $NH_2^-$ and $NR_3$, where R is hydrogen or methyl; L is a ligand which is a 9 to 12 membered ring containing at least three nitrogen atoms forming a portion of the ring which coordinate to a manganese centre; Z represents the charge of the complex and is an integer which may be positive or negative; Y is a monovalent or multivalent counterion leading to charge neutrality, which is dependent upon the charge z of the complex; and q=z/(charge Y), the process comprising the steps of (i) reacting a Mn (III) salt with at least an equivalent amount of a compound comprising the ligand L to form said manganese complex where manganese is in the III oxidation state characterized in that the reaction is carried out in a non-aqueous polar solvent containing less than 0.5% by weight of water; and (ii) oxidizing the manganese complex formed in step (i) with an oxidizing agent selected from the group consisting of pure oxygen and hydrogen peroxide to thereby form the manganese complex where manganese is in the IV oxidation state.

2. A process according to claim 1 wherein the non-aqueous solvent is acetonitrile.

3. A process according to claim 1 wherein step (i) is carried out in the presence of a mineral acid having a pKa<0.

4. A process according to claim 3 wherein the ratio of mineral acid to the ligand, in the ligand containing compound, is from 0.1:10 to 0.5 to 5.

5. A process according to claim 1 wherein the compound comprising the ligand and used in step (i) is in the form an acid salt of the ligand.

6. A process according to claim 1 wherein a stabilizer for Mn(III) compound and an acid scavenger which is sodium bicarbonate are added to the reaction.

7. A process according to claim 1 wherein the Mn(III) salt used in step (i) is obtained by oxidation of a corresponding Mn(II) salt with an oxidising agent prior to or during said step (i).

8. A process according to claim 1 wherein the ligand is 1,4,7-trimethyl-1,4,7-triazacyclononane.

9. A process according to claim 8 wherein the Mn(III) salt is an acetate.

10. A process according to claim 9 wherein the manganese complex of step (i) has one X that is $O_2^-$ and two other X that are acetate.

11. A process according to claim 10 wherein the oxidized manganese complex of step (ii) has all X that are oxygen.

* * * * *